United States Patent [19]
Wu et al.

[11] Patent Number: 5,696,101
[45] Date of Patent: Dec. 9, 1997

[54] OXIDIZED CELLULOSE AND VITAMIN E BLEND FOR TOPICAL HEMOSTATIC APPLICATIONS

[75] Inventors: Stephen Hong-Wei Wu, Kingsport; Warren Kent Hopkins, Piney Flats, both of Tenn.

[73] Assignee: Eastman Chemical Company, Kingsport, Tenn.

[21] Appl. No.: 633,272

[22] Filed: Apr. 16, 1996

[51] Int. Cl.$^6$ .................. A61K 31/715; A61K 31/355
[52] U.S. Cl. .................................... 514/57; 514/458
[58] Field of Search ............................ 514/57, 458

[56] References Cited

U.S. PATENT DOCUMENTS 2,642,375  6/1953  Henderson et al. .

FOREIGN PATENT DOCUMENTS 216378  4/1987  European Pat. Off. .
2852319  6/1979  Germany .

OTHER PUBLICATIONS

Singh et al, Biomater. Med. Devices Artif. Organs, 7(4), 495–512 (1979).

Pierce et al, J. Oral Pathol. (Denmark), 13(6), 661–70 (1984).

Mattsson et al, Swed. Dent. J. (Sweden), 13(2), 57–62 (1990).

Dimitrijevich et al, Carbohydrate Res 198(2), 331–41 (1990).

Derwent Abstract No. 89–12193, Jandak et al., Blood, 73, No. 1, pp.141–149, 1989.

Embase Abstract No. 77084859, Fong, Experientia (Switzerland), 32/5, pp. 639–641, 1976.

Sedbase Abstract No. 00257906, Steiner, Thromb–Haemostasis, 49/2, pp. 73–77, 1983.

Sedbase Abstract No. 00257906, Srivastava, Prostaglandins–Leukotrienes–med., 21/2, pp. 177–185, 1986.

*Primary Examiner*—Raymond Henley, III
*Attorney, Agent, or Firm*—Andrew B. Griffis; Harry J. Gwinnell

[57] ABSTRACT

The present invention relates to a hemostatic composition comprising 1 to 90 weight percent of vitamin E or a derivative of vitamin E, 1 to 95 weight percent of oxidized cellulose, and 0.1 to 75 weight percent of water. The hemostatic composition may be formed into pellets, powder, paste, gum, gel, or liquid suitable for molding to conform to the contours of a wound.

15 Claims, 4 Drawing Sheets

1

OXIDIZED CELLULOSE AND VITAMIN E BLEND FOR TOPICAL HEMOSTATIC APPLICATIONS

FIELD OF THE INVENTION

The present invention relates to a hemostatic composition comprising 1 to 90 weight percent of vitamin E or a derivative of vitamin E, 1 to 95 weight percent of oxidized cellulose, and 0.1 to 75 weight percent of water.

BACKGROUND OF THE INVENTION

Four materials which are commonly used as hemostatic agents following surgery to control bleeding and oozing of fluids from wounds include thrombin, absorbable gelatin, microfibrillar collagen, and oxidized cellulose. Thrombin, commonly available as a powder derived from bovine sources, is a very effective clotting agent, but it may cause allergic reactions in sensitive individuals. Absorbable gelatin, available as sponges, packs, dental packs, or prostatectomy cones, is capable of absorbing and holding many times its weight of whole blood, and is absorbed completely by the body within four to six weeks. However, its use in the presence of infection is not recommended because it may form a nidus of infection and abscess formation.

Microfibrillar collagen is an absorbable topical hemostatic agent prepared as a dry sterile, fibrous, water insoluble, partial hydrochloric acid salt of purified bovine corium collagen. While microfibrillar collagen does not generally initiate wound infections, it may promote infection, including abscess formation, and as an animal product, may promote allergic or foreign body reactions.

Oxidized cellulose, is available under the trade name Oxycel™ from Becton Dickinson Co. Oxidized cellulose is soluble in, or swollen by, fluids from wounds, forming a sticky mass which adheres readily and stops bleeding or the oozing of fluids from open wounds or surgical incisions, and is eventually absorbed by the body. Oxidized cellulose shows bactericidal effect against a wide range of pathogenic microorganisms. In addition, the biocompatibility and biodegradability of oxidized cellulose in vivo has been studied by Singh et al, *Biomater. Med. Devices Artif. Organs*, 7(4), 495–512(1979); Pierce et al, *J. Oral Pathol.* (Denmark), 13(6), 661–70 (1984); Mattsson et al, *Swed. Dent. J.* (Sweden), 13(2), 57–62(1990); and Demitrijevich et al, *Carbohydrate Res* 198(2), 331–41 (1990). The studies concluded that neither oxidized cellulose nor its degradation products are detrimental to either the healing process or the organism in general.

Oxidized cellulose is only available in solid forms such as pads, pladgets, or strips which, though soluble in mild bases, are not soluble in water. Oxidized cellulose does not form a paste in contact with water alone and it is reported that the hemostatic action is reduced by moistening with water or saline.

U.S. Pat. No. 2,642,375 discloses a hemostatic composition comprising polyethylene glycol, of average molecular weight approx. 1500, and finely divided oxidized cellulose intimately mixed together.

European Patent App. 216,378 discloses hemostatic material based on fibrous particles of carboxycellulose and its alkali or calcium salts, and is characterized by the fact that the fibrous particles of the hemostatic agent are bonded physically or physico-chemically with particles of an adhesive to form a spatially crosslinked structure.

DE 2,852,319 discloses an absorbable, semisolid, hemostatic mass for use in prevention of bone hemorrhages which contains a mixture of fibrin and collagen powder in a water-soluble, biotolerable foundation, and an adhesive selected from polyglucoside, gelatin, polyvinylpyrrolidone, cellulose esters, oxidized cellulose, and water-soluble starch or sugars.

SUMMARY OF THE INVENTION

The topical hemostatic composition of the present invention can be used in the form of pellets, powder, paste, gum, gel, or liquid which can be spread over a wound, or molded into a shape which conforms to the contours of the wound. The topical hemostatic composition comprises:

(A) 1 to 90 weight percent of vitamin E or a derivative of vitamin E;

(B) 1 to 95 weight percent of oxidized cellulose; and (C) 0.1 to 75 weight percent water, wherein the weight percents are based on the total weight of the hemostatic composition.

BRIEF DESCRIPTION OF THE DRAWINGS

The invention will be more fully understood and further advantages will become apparent when reference is made to the following detailed description of the invention and the accompanying drawings in which.

DESCRIPTION OF THE INVENTION

Figure 1:
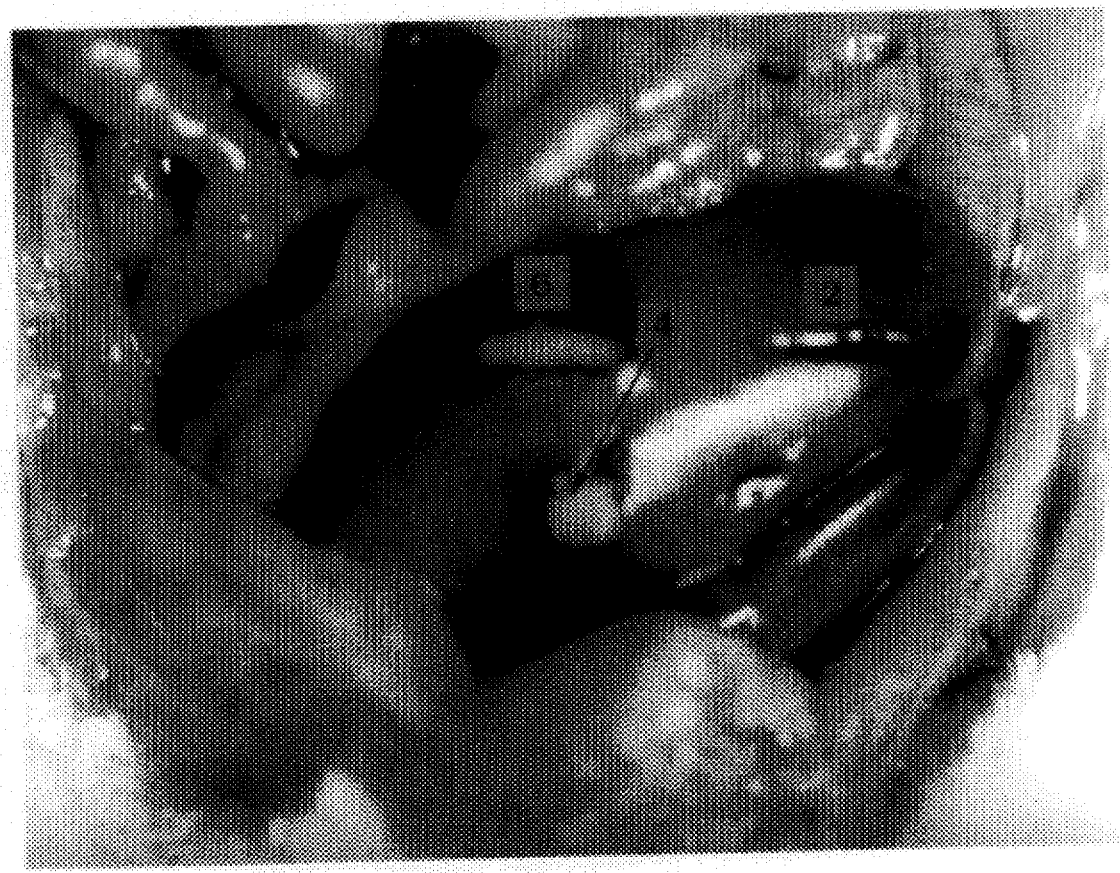
FIG. 1 is a photograph of an exposed rat liver containing three incisions. Incision 2 was untreated. Incision 4 was treated with a hemostatic composition containing 42 weight percent of d-α-tocopheryl polyethylene glycol 1000 succinate, 58 weight percent of oxidized cellulose, and about 0.1 weight percent of water in the form of a pellet. Incision 6 was treated with a hemostatic composition containing 37.5 weight percent of d-α-tocopheryl polyethylene glycol 1000 succinate, 51.8 weight percent of oxidized cellulose, and about 10.7 weight percent of water in the form of a paste.

The first component, component (A), of the topical hemostatic composition is vitamin E. As used herein, the term "vitamin E" refers to α, β, γ, and δ-tocopherol and their derivatives. The vitamin E may also be a combination of α, β, γ, and δ-tocopherols. The α-form occurs naturally as the d-isomer known as d-α-tocopherol (d-2,5,7,8-tetramethyl-2-(4',8',12'-trimethyltridecyl)-6-chromanol). Other forms of vitamin E which can be used include: d-α-tocopheryl acetate, d-α-tocopheryl succinate, d-α-tocopheryl nicotinate and d-α-tocopheryl linoleate. Also the corresponding dl forms may be used which include: dl-α-tocopherol, dl-α-tocopheryl acetate, dl-α-tocopheryl succinate, dl-α-tocopheryl nicotinate and dl-α-tocopheryl linoleate and their derivatives. The vitamin E is present in an amount ranging from 1 to 90 weight percent, preferably 20 to 80 weight percent of the total topical hemostatic composition.

An especially preferred vitamin E derivative is d-α-tocopheryl polyethylene glycol 1000 succinate (TPGS), a water-soluble vitamin E form with surfactant activity. TPGS is prepared by the esterification of vitamin E succinate with polyethylene glycol wherein the polyethylene glycol has a number average molecular weight of 300 to 6000, preferably about 1000. TPGS has a hydrophilic lipophilic balance of 15–19, and acts as an emulsifier for lipophilic substances, including drugs. Moreover, the addition of TPGS to a drug dosage may enhance the bioavailability of the drug. TPGS is commercially available from Eastman Chemical Company.

The second component, component (B), of the topical hemostatic composition is oxidized cellulose. Oxidized cellulose refers to cellulose specifically oxidized and containing carboxylic groups. The preferred form of oxidized cellulose contains a carboxylic group in the $C_6$ carbon. Oxidized cellulose is available from Eastman Chemical Company.

Oxidized cellulose has hemostatic properties and aids in stopping bleeding. In addition, oxidized cellulose may be degraded by enzymes of the carbohydrase system and thus it is biodegradable and part of it may be absorbed in the tissue without adverse effects. The incorporation of oxidized cellulose in wounds is helpful in absorbing fluids and aids healing. The combination of oxidized cellulose and vitamin E and/or its derivatives, is particularly effective in helping directly to stop bleeding, and indirectly aids healing by reducing and inflammation, itching and the severity of scars. The preferred range of oxidized cellulose in the composition is 5 to 90 weight percent based on the total topical hemostatic composition. If the amount of oxidized cellulose is too low, the hemostatic effect of the resulting gel will be reduced.

The third component, component (C), of the topical hemostatic composition is water. Water may be distilled or tap water. Distilled water is preferred because it is free of metals, odors, and microbes.

Optionally, the topical hemostatic compositions may include bioactive materials, growth factors, plasticizing agents, opacifiers, surfactants, fragrances, sunscreens, antifungals, antibiotics, insect repellents, preservatives, emollients, humectants, antioxidants, thickeners, moisturizers, astringents, deodorants, as well as other compatible materials which may be desired to enhance the properties of the compositions. The optional ingredients may be present in widely varying amounts depending upon the particular ingredients selected and the results desired.

Examples of suitable bioactive materials include the following: growth promoters, growth factors such as glucan, hyaluronic acid, antioxidants such as beta-carotene, pain relievers such as lidocaine, benzocaine, and bupivacaine; antibiotics such as penicillin, cephalosporin, vancomycin, and bacitracin; anti-bacterials such as sulfanilamide, sulfacetamide, sulfadiazine, and pyrimethamine; and vitamins and vitamin derivatives (in addition to vitamin E), such as vitamin A, vitamin D, vitamin C, thiamine, riboflavin, and niacin. Two or more bioactive materials may be used in the same topical hemostatic composition, provided the bioactive materials do not react adversely with each other.

The topical hemostatic compositions of the present invention may be applied to a wound located anywhere on the body where wound treatment is desired, by smoothing it over the wound. The topical hemostatic compositions may also be formed into pellets or a paste suitable for molding to conform to the contours of a wound or extruded, for example through an instrument used for laparoscopic surgery, directly onto a wound. The topical hemostatic compositions reduce inflammation, swelling, and itching, promote wound healing, and reduce scarring.

The topical hemostatic compositions of the present invention are prepared by mixing oxidized cellulose with vitamin E and water, and if desired, an effective amount of pharmaceutically active agents. Mixing of the ingredients may be done in any convenient manner, and will depend upon the properties of the bioactive material which is added in addition to the vitamin E and oxidized cellulose. For example, oxidized cellulose and vitamin E may be ground together cryogenically with dry ice or another cooling agent such as liquid nitrogen to give a powder which may then be blended with the bioactive material. Alternatively, oxidized cellulose and the bioactive material may be added to molten vitamin E with thorough mixing, and the resulting mixture may be ground cryogenically to a powder. In either case, the powder may be readily formed into a convenient form for use, such as into pellets, paste, powder, or tablets.

The method for mixing the components will depend upon the characteristics and stability of any bioactive compound which is added to the oxidized cellulose-vitamin E mixture. The blend of vitamin E and oxidized cellulose may be mixed with water to give a paste of the desired consistency. Alternatively oxidized cellulose powder may be blended into a solution or gel form of vitamin E in water.

A particularly useful application for the topical hemostatic composition is in the form a paste which may be spread over or shaped to conform to the contours of a wound. In bone surgery, for example, broken or cut bones are frequently covered with a stiff "bone wax". The primary function of bone wax is to prevent bleeding from broken bone ends. The material used for this purpose at present, beeswax with isopropyl palmitate, is not absorbed by the body, and it does not completely prevent oozing of blood and other fluids from the break. In contrast, a waxy paste prepared using TPGS, oxidized cellulose and if desired, a small amount of water, is completely absorbed by the body as the bone heals.

In another embodiment of the invention, the proportions of vitamin E, oxidized cellulose, water, and bioactive ingredients are chosen so that the resulting thin paste or gel may be extruded, for example through an instrument used for laparoscopic surgery, directly onto a wound.

The following examples are intended to illustrate, but not limit, the scope of this invention. All percentages in the examples are on a weight bases unless otherwise stated.

EXAMPLE 1

This example illustrates the preparation of a hemostatic composition in the form of a powder suitable for topical application to wounds.

Oxidized cellulose powder (11.6 grams) was added to 8.4 grams of molten TPGS. The mixture contained at least 0.1 weight percent of water. The mixture was stirred until cool, blended thoroughly in a mortar and pestle, then ground with dry ice to produce a fine powder, which was dried in a vacuum desiccator.

EXAMPLE 2

This example illustrates the preparation of a paste of TPGS and oxidized cellulose.

TPGS (800.8 grams) was heated to 85° C. and 200.4 grams of boiling water was added slowly in small portions. The mixture was stirred vigorously and allowed to cool to room temperature to form a hard, clear gel. The gel (16.7 grams) was added in small portions to 12 grams of oxidized cellulose powder, with grinding in a mortar and pestle after each addition. The resulting mass was kneaded to complete homogenization. The resulting paste exhibited the consistency of dough or putty, and may readily be shaped to conform to either internal or external wounds. Twelve samples of oxidized cellulose/TPGS/water mixtures were prepared and their characteristics were evaluated. The results are summarized in Table I.

TABLE II

|  | Control | TPGS | Oxidized Cellulose | TPGS + Ox. Cell. |
| --- | --- | --- | --- | --- |
| Body Wt., g. | 322 ± 5 | 320 ± 9 | 324 ± 8 | 321 ± 7 |
| Blood Lost, g. | 3.19 ± 1.25 | 2.33 ± 1.33 | 2.19 ± 1.05 | 1.96 ± 1.12 |
| Bleed. Time, Sec. | 364 ± 170 | 266 ± 143 | 276 ± 88 | 174 ± 52 |

The test results in Table II indicate that although there was notable reduction in both bleeding time and blood loss when either TPGS or oxidized cellulose was used alone, the effect of the combination of the two is statistically significant ($p<0.05$).

EXAMPLE 4

Three incisions were made in a rat liver as shown in FIG. 1. Incision 2 was untreated. Extensive bleeding occurred at the untreated incision. Incision 4 was treated with a hemostatic composition containing 42 weight percent of d-α-tocopheryl polyethylene glycol 1000 succinate, 58 weight

TABLE I

Compositions and Characteristics of Oxidized Cellulose /TPGS/Water Blends

| Sample No. | TPGS/H$_2$O Gel Composition | Composition (g) Oxicell/ (TPGS/H$_2$O Gel) | Composition (g) Oxicell/ TPGS/H$_2$O | Composition (%) Oxicell/ TPGS/H$_2$O | Characteristics |
| --- | --- | --- | --- | --- | --- |
| 1 | 90/10 | 8.04/(09.03) | 8.04/08.37/00.93 | 46.03/48.3/5.36 | Malleable/Staff |
| 2 | 80/20 | 8.00/(11.04) | 8.00/08.83/02.20 | 42.00/46.4/11.6 | Malleable |
| 3 | 60/40 | 8.02/(19.45) | 8.02/11.67/07.78 | 29.02/42.5/28.3 | Waxy, Pliable Gum |
| 4 | 40/60 | 8.01/(18.47) | 8.01/07.39/11.08 | 30.02/27.9/41.8 | Gel |
| 5 | 30/70 | 8.00/(24.64) | 8.00/07.39/17.25 | 24.05/22.6/52.8 | Gel-Wet Dough Consistency |
| 6 | 20/80 | 8.00/(36.09) | 8.00/07.38/29.05 | 17.08/16.4/65.7 | Thick Liquid |
| 7 | 90/10 | 8.00/(36.41) | 8.00/32.77/03.64 | 18.01/73.8/8.20 | Flowable Liquid |
| 8 | 80/20 | 8.02/(41.11) | 8.02/32.89/08.22 | 16.03/66.9/16.7 | Waxy, Melts When Touched |
| 9 | 60/40 | 4.02/(27.29) | 4.02/16.37/10.92 | 12.09/52.3/34.9 | Gel |
| 10 | 40/60 | 2.01/(20.24) | 2.01/08.10/12.14 | 09.03/36.4/54.6 | Gel |
| 11 | 30/70 | 2.00/(26.69) | 2.00/08.01/18.68 | 06.97/27.9/65.1 | Sticky Paste |
| 12 | 20/80 | 2.02/(42.98) | 2.02/08.60/34.38 | 04.48/19.1/76.4 | Colloidal Solution |

The results in Table I clearly indicate that all of the compositions were hemostatic. In addition, Sample Nos. 2, 3, and 4 exhibited the best handling properties in terms of ease of wound application.

EXAMPLE 3

This example compares the effectiveness of the combination of TPGS with oxidized cellulose with that of either component alone, and with a control.

Operations were performed on four groups of ten rats each, as indicated in Table II. Identical incisions were made across the width of the kidneys, which were then treated with 0.2 grams of powdered hemostatic compositions as described in Table II. Total blood loss and time until bleeding stopped are summarized in Table II.

percent of oxidized cellulose, and about 0.1 weight percent of water in the form of a pellet. No bleeding occurred at incision 4. Incision 6 was treated with a hemostatic composition containing 37.5 weight percent of d-α-tocopheryl polyethylene glycol 1000 succinate, 51.8 weight percent of oxidized cellulose, and about 10.7 weight percent of water in the form of a paste. No bleeding occurred at incision 6.

EXAMPLE 5

Figure 2:
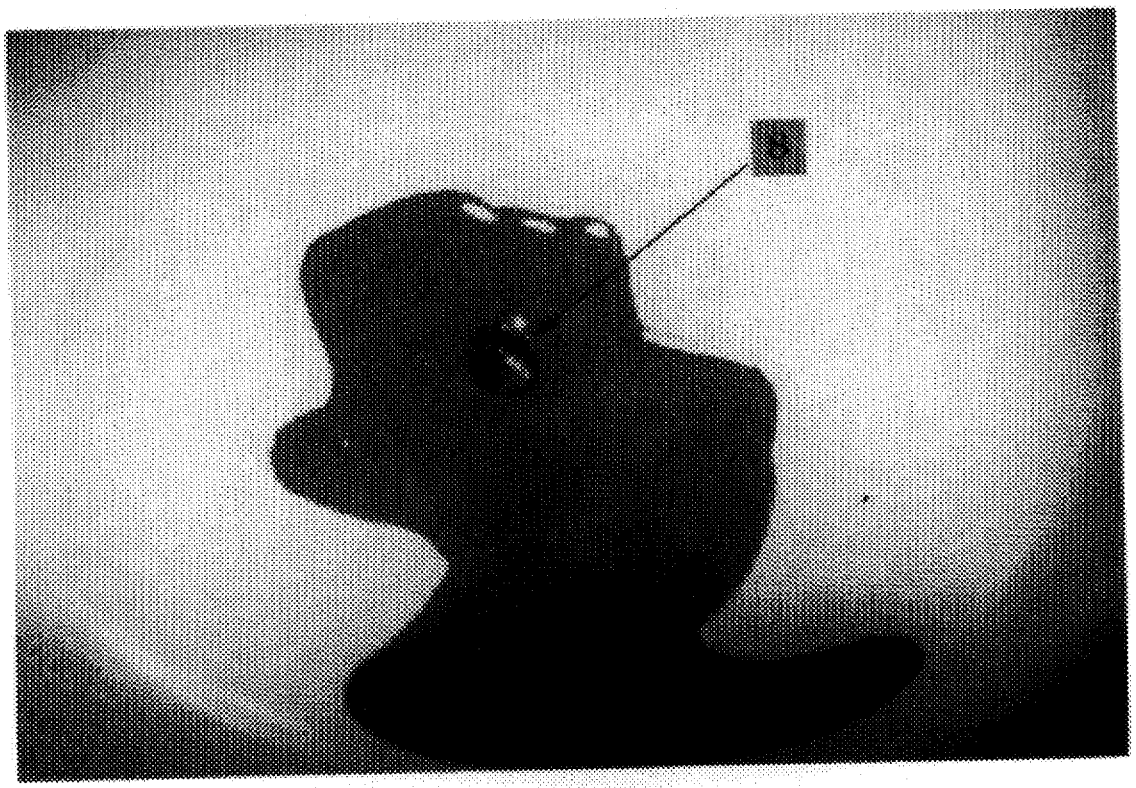
FIG. 2 is a photograph of a pool of fresh blood with a hemostatic composition 8 containing 42 weight percent of d-α-tocopheryl polyethylene glycol 1000 succinate, 58 weight percent of oxidized cellulose, and about 0.1 weight percent of water in the form of a pellet.

A hemostatic composition containing 42 weight percent of d-α-tocopheryl polyethylene glycol 1000 succinate, 58 weight percent of oxidized cellulose, and about 0.1 weight percent of water in the form of a pellet was placed into a pool of fresh blood as shown in FIG. 2. Clotting occurred at the point of contact of the blood with the pellet and, to some extent, on the surface of the pool. There was no massive clotting of the entire pool of blood.

EXAMPLE 6

Figure 3:
FIG. 3 is a photograph of freshly cut bone of an animal. Sections 10, 14, and 18 were untreated. Section 12 was treated with a commercial bone wax. Section 16 was treated with a hemostatic composition in malleable form containing 46.4 weight percent of d-α-tocopheryl polyethylene glycol 1000 succinate, 42.0 weight percent of oxidized cellulose, and about 11.6 weight percent of water. Section 20 was treated with a sterilized hemostatic composition in malleable form containing 46.4 weight percent of d-α-tocopheryl polyethylene glycol 1000 succinate, 42.0 weight percent of oxidized cellulose, and about 11.6 weight percent of water.

A bone was cut as shown in FIG. 3. Sections 10, 14, and 18 were untreated. Massive bleeding occurred at the untreated portion of bone. Section 12 was treated with a commercial bone wax. The bone wax allowed blood to ooze through the coating of bone wax. Section 16 was treated with a hemostatic composition in malleable form containing 46.4 weight percent of d-α-tocopheryl polyethylene glycol 1000 succinate, 42.0 weight percent of oxidized cellulose, and about 11.6 weight percent of water. Section 20 was treated with a sterilized hemostatic composition heated in an autoclave at 115° C.–120° C. for about 30 minutes. The hemostatic composition in malleable form contained 46.4 weight percent of d-α-tocopheryl polyethylene glycol 1000 succinate, 42.0 weight percent of oxidized cellulose, and about 11.6 weight percent of water. The sections covered with the topical hemostatic compositions showed no bleeding.

EXAMPLE 7

This example is similar to Example 6, except that the animal had been treated with an anticoagulant, which retards clotting.

Figure 4:
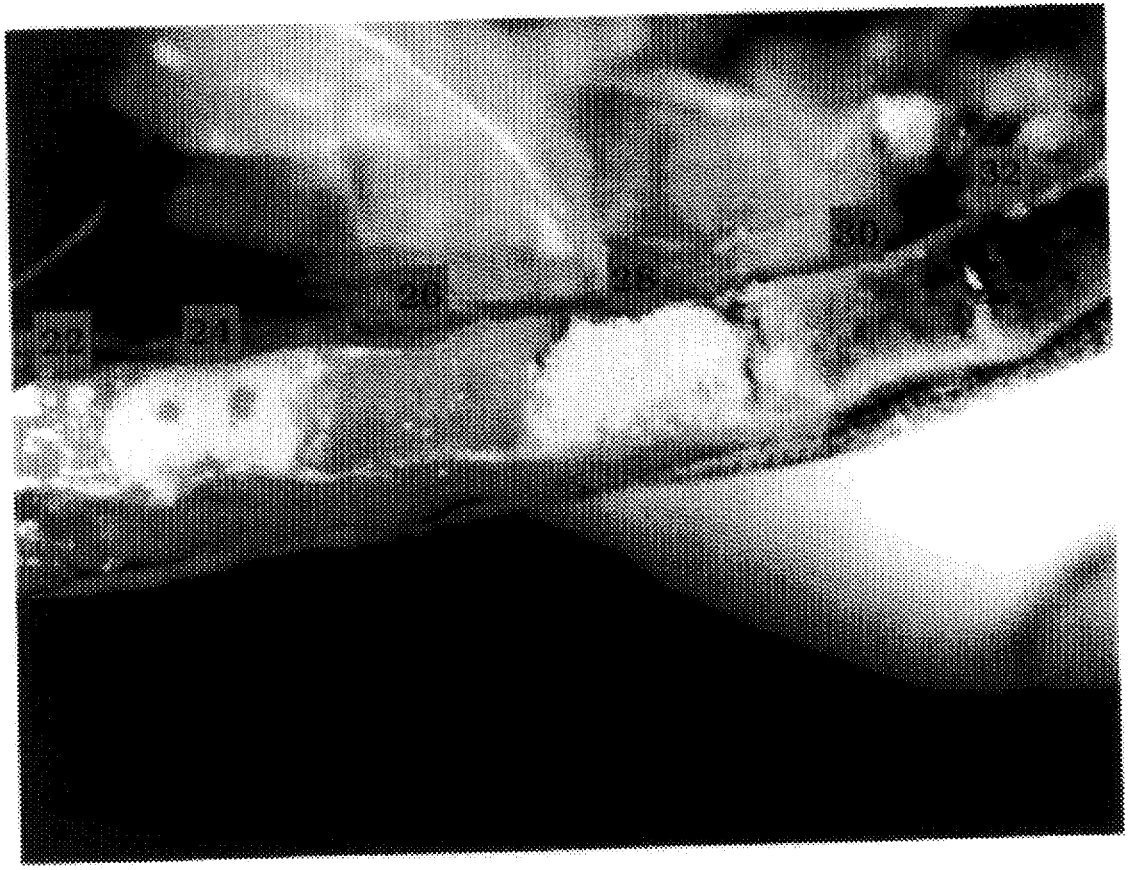
FIG. 4 is a photograph of freshly cut bone of an animal to which an anticoagulant had been administered. Sections 22, 26, and 30 were untreated. Section 24 was treated with a commercial bone wax. Section 28 was treated with a hemostatic composition in malleable form containing 46.4 weight percent of d-α-tocopheryl polyethylene glycol 1000 succinate, 42.0 weight percent of oxidized cellulose, and about 11.6 weight percent of water. Section 32 was treated with a sterilized hemostatic composition in malleable form containing 46.4 weight percent of d-α-tocopheryl polyethylene glycol 1000 succinate, 42.0 weight percent of oxidized cellulose, and about 11.6 weight percent of water.

A bone was cut as shown in FIG. 4. Sections 22, 26, and 30 were untreated. Massive bleeding occurred at the untreated portion of bone. Section 24 was treated with a commercial bone wax. The bone wax allowed blood to ooze through the coating of bone wax. Section 28 was treated with a hemostatic composition in malleable form containing 46.4 weight percent of d-α-tocopheryl polyethylene glycol 1000 succinate, 42.0 weight percent of oxidized cellulose, and about 11.6 weight percent of water. Essentially no bleeding occurred at Section 28. Section 32 was treated with a sterilized hemostatic composition heated in an autoclave at 115° C.–120° C. for about 30 minutes. The hemostatic composition in malleable form contained 46.4 weight percent of d-α-tocopheryl polyethylene glycol 1000 succinate, 42.0 weight percent of oxidized cellulose, and about 11.6 weight percent of water. No bleeding occurred at Section 32.

Many variations will suggest themselves to those skilled in this art in light of the above detailed description. All such obvious modifications are within the full intended scope of the appended claims.

What is claimed is:

1. A topical hemostatic composition comprising:
   (A) 1 to 90 weight percent of vitamin E or a derivative of vitamin E;
   (B) 1 to 95 weight percent of oxidized cellulose; and
   (C) 0.1 to 75 weight percent water, wherein the weight percents are based on the total weight of the hemostatic composition.

2. A topical hemostatic composition comprising:
   (A) 1 to 90 weight percent of a polyethylene glycol ester of vitamin E succinate;
   (B) 1 to 95 weight percent of oxidized cellulose; and
   (C) 0.1 to 75 weight percent water, wherein the weight percents are based on the total weight of the hemostatic composition.

3. The topical hemostatic composition according to claim 1 wherein the vitamin E is selected from the group consisting of α, β, γ, and δ-tocopherol, and combinations thereof.

4. The topical hemostatic composition according to claim 3 wherein the vitamin E is selected from the group consisting of d-α-tocopherol, d-α-tocopheryl acetate, d-α-tocopheryl succinate, d-α-tocopheryl nicotinate, d-α-tocopheryl linoleate, and combinations thereof.

5. The topical hemostatic composition according to claim 3 wherein the vitamin E is selected from the group consisting of dl-α-tocopherol, dl-α-tocopheryl acetate, dl-α-tocopheryl succinate, dl-α-tocopheryl nicotinate, dl-α-tocopheryl linoleate, and combinations thereof.

6. The topical hemostatic composition according to claim 1 which additionally contains at least one bioactive material.

7. The topical hemostatic composition according to claim 6 wherein the bioactive material is selected from the group consisting of pain relievers, growth promoters, growth factors, antibiotics, anti-bacterials, vitamins and vitamin derivatives, and combinations thereof.

8. The topical hemostatic composition according to claim 7 wherein the bioactive material is selected from the group consisting of glucan, hyaluronic acid, lidocaine, benzocaine, bupivacaine, penicillin, cephalosporin, vancomycin, bacitracin, sulfanilamide, sulfacetamide, sulfadiazine, pyrimethamine, vitamin A, vitamin D, vitamin C, thiamine, riboflavin, niacin, beta-carotene, and combinations thereof.

9. The topical hemostatic composition according to claim 8 wherein the bioactive material is selected from the group consisting of glucan, hyaluronic acid, and beta-carotene.

10. A composition comprising 1 to 90 weight percent of vitamin E or a derivative of vitamin E, 1 to 95 percent of oxidized cellulose, and 0.1 to 75 weight percent water, wherein the weight percents are based on the total weight of the composition.

11. The composition according to claim 10, wherein vitamin E or a derivative of vitamin E is present in an amount ranging from 20 to 80 weight percent of the total composition.

12. The composition according to claim 10, wherein the vitamin E or derivative of vitamin E is TPGS.

13. The composition according to claim 10, wherein oxidized cellulose is present in the amount of 5 to 90 weight percent, based on the total composition.

14. The composition according to claim 10, further comprising a bioactive material selected from the group consisting of growth promoters, growth factors, antioxidants, pain relievers, antibiotics, anti-bacterials, vitamins other than vitamin E, and mixtures thereof.

15. The composition according to claim 14, wherein said composition is in the form of an extrudable thin paste or gel.

* * * * *

UNITED STATES PATENT AND TRADEMARK OFFICE
CERTIFICATE OF CORRECTION

PATENT NO. : 5,696,101
DATED : December 9, 1997
INVENTOR(S) : Stephen Hong-Wei Wu, Warren Kent Hopkins It is certified that error appears in the above-identified patent and that said Letters Patent is hereby corrected as shown below:

Title page: Item [56]    delete "13(2)" and insert therefor ---14---.

Column 1, line 44, delete "13(2)" and insert therefor ---14---.

Signed and Sealed this

Tenth Day of November 1998

Attest:

BRUCE LEHMAN

*Attesting Officer*        *Commissioner of Patents and Trademarks*